United States Patent [19]

Hunter

[11] Patent Number: 4,865,972
[45] Date of Patent: Sep. 12, 1989

[54] ANTIBODY-BASED BIOASSAY FOR ENZYME-INDUCING CHEMICALS

[75] Inventor: Kenneth W. Hunter, Potomac, Md.

[73] Assignee: Westinghouse Electric Corp., Pittsburgh, Pa.

[21] Appl. No.: 899,011

[22] Filed: Aug. 22, 1986

[51] Int. Cl.$^4$ .................... G01N 53/00; C12Q 1/02
[52] U.S. Cl. .......................... 435/7; 435/25; 435/29
[58] Field of Search ................. 435/7, 25, 29

[56] References Cited

PUBLICATIONS

Nebert and Negishi, *Biochemical Pharmacology*, 31: 2311–2317 (1982).
Klotz et al., *Anal. Bioch.*, 140: 138–145 (1984).
Prough et al., in Meth. Enzymol., Fleischer and Packer (Eds.) 52 C:372–377 (1978).
*National Dioxin Study*, Environmental Protection Agency (EPA/600/385/019), Apr. 1985.
Albro et al., *Meth. Enzymol.*, Langone and vanVunakis, Eds., vol. 84, pp. 619–628, (Academic Press, New York, 1982).
Albro et al., Toxicol. Appl. Pharmacol., 50: 137–146 (1979).
Bradlaw and Casterline, J. Assoc. Off. Anal. Chem., 62: 904–916 (1979).
Kennel et al., *Toxicology and Applied Pharmacology*, 82: 256–263 (1986).
Johnson, "*Multiple Forms of Cytochrome P-450: Criteria and Significance*", in Reviews and Biochemical Toxicology, Hodgson et al., Eds. (Elsevier North Holland, Inc. 1979), pp. 1–26.

*Primary Examiner*—Robert J. Warden
*Assistant Examiner*—Robert Benson
*Attorney, Agent, or Firm*—Joyce L. Morrison

[57] ABSTRACT

An antibody-based bioassay for enzyme-inducing chemicals is disclosed. The percent induction of an enzyme or class of related enzymes in living cells by an enzyme-inducing chemical in a sample is determined before and after the addition to the sample of an antibody to the chemical. The concentration of the chemical before and after the addition of the antibody is determined by comparison to the percent induction by known concentrations of the chemical. This permits the determination of the concentration of the chemical in the sample.

16 Claims, 2 Drawing Sheets

ANTIBODY-BASED BIOASSAY FOR ENZYME-INDUCING CHEMICALS

BACKGROUND OF THE INVENTION

This invention relates to bioassays and more specifically to an antibody-based bioassay for enzyme-inducing chemicals.

Many xenobiotic compounds (compounds not normally found in an animal body) induce the formation in animal cells of enzymes which detoxify or modify such compounds. The results of the detoxification process, in most cases, is facilitated excretion of the offending compound A major source of xenobiotic modification in mammalian cells is the microsomal mixed-function oxidase system, a chain of enzymes terminating in one of a family of enzymes known as the cytochromes P-450. It is these terminal cytochromes that actually interact with the xenobiotic compound and chemically alter or metabolize it.

The spectrum of xenobiotic compounds which can be acted upon by the microsomal mixed-function oxidase system is extremely diverse. Studies designed to investigate the source of this diversity have demonstrated that it originates in the terminal cytochromes themselves. There are actually multiple forms of cytochrome P-450, each acting upon a group of loosely related chemical types. The form of cytochrome P-450 needed to interact with a xenobiotic compound is determined when that compound presents itself within the living cell. The cell responds to the presence of this foreign compound by increasing the synthesis of the appropriate cytochrome. This increase in cytochrome concentration in response to the presence of a specific chemical is referred to as induction.

The two forms of the terminal cytochrome relevant to this invention have been given the names cytochrome $P_1$-450, also known as alkyl hydrocarbon hydroxylase, and cytochrome P-448, otherwise referred to as aryl hydrocarbon hydroxylase. As used herein, the alkyl or aryl hydrocarbon hydroxylase designations refer to the type of enzymatic activity or substrate preferences associated with the induction of these enzymes. As also used herein, the abbreviation "AHH" will refer to either alkyl or aryl hydrocarbon hydroxylase, each of which is, in fact, a group of related enzymes.

In the presence of polycyclic aromatic hydrocarbons (aryl hydrocarbons) cytochrome P-448 concentration and activity increases in cells. When compounds such as the barbituates are present (hydrocarbons with less aryl or benzene-like character), cytochrome $P_1$-450 is increased. Thus increasing the induction of these enzymes by particular chemicals, for example by exposing cultured cells to samples containing various concentrations of one or the other types of inducers, provides a basis for detecting and measuring these chemicals in various kinds of samples.

The AHH enzymes are inducible enzymes, that is, their activity is increased in the presence of alkyl or aryl hydrocarbons. An AHH-inducing chemical rapidly penetrates the membrane of a living cell, and once within the cytoplasm, it interacts with a binding protein to form a complex. The complex is rapidly translocated into the nucleus of the cell, where it binds to a specific site on DNA. This binding serves as a signal for transcription of the adjacent DNA into messenger RNA that codes for AHH enzymes. This messenger RNA is rapidly translocated into the cell cytoplasm, where it is translated into AHH enzymes. The enzymes modify or detoxify toxic chemicals.

The complex also activates a second group of genes that code for proteins that control cell proliferation and differentiation. Activation of these genes can lead to cancerous transformation, a known property of many AHH inducers. Other AHH inducers are extremely toxic or harmful in other ways to living cells and organisms. Thus, measuring the induction of AHH by particular chemicals provides a basis for detecting and measuring the concentrations of these chemicals in various kinds of samples.

The level of AHH induction can be measured by measuring any of the AHH enzymes 7-Ethoxyresorufin-O-deethylase (EROD) one of the cytochrome $P_1$-450 enzymes, is conveniently used because the substrate, 7-ethoxyresorufin, is minimally toxic and the product, resorufin, can be measured spectrophotometrically at 572 nm according to the method of Klotz et al., *Anal. Bioch.*, 140: 138–145 (1984), which is incorporated herein by reference, or fluorimetrically as described by Prough, et al. *Meth. Enzymol.*, 52C: 372–377 (1978) which is incorporated herein by reference.

AHH inducers include the dibenzodioxins, dibenzofurans, and biphenyls. Polychlorinated dibenzodioxins have been the focus of much scientific and regulatory attention because of their extreme toxicity to experimental animals and their possible hazard to human beings. They occur as by-products and impurities in the production of chlorinated phenols and their conversion products, such as the phenoxy-acetic acid herbicides. The most toxic compound of this group known to date is 2,3,7,8-tetrachloro-dibenzo-p-dioxin (TCDD). Because of the toxicity of TCDD, it is desirable to detect it in the low parts per quadrillion range.

The present methods for detecting TCDD and related chemicals generally involve some form of low or high resolution chromatography, usually gas chromatagraphy, and high or low resolution mass spectrometry. (See Environmental Protection Agency Publication EPA/600/3-85/019, April 1985, entitled the *National Dioxin Study*.) This technology requires very expensive, sophisticated equipment, a high degree of skill on the part of the person running the assay, and a significant amount of time. Thus, it costs as much as $1,000–3,000 to test a sample for the presence of TCDD. In addition, this technique leaves much to be desired in terms of sensitivity. The lowest concentration of TCDD detectable is approximately 1 part per trillion.

Antibody detection techniques could significantly lower the cost and time associated with the detection of TCDD and similar chemicals. However, such techniques are limited by their sensitivity. One antibody technique, radioimmunoassay, has been proposed as a means of detecting TCDD in the low parts per trillion range Albro et al., *Methods in Enzymology*, 84: 619–628 (1982); Albro et al., *Toxicol. Appl. Pharmacol.*, 50: 137–146 (1979). However, radioimmunoassay is still not sufficiently sensitive to detect concentrations of TCDD below 10 parts per trillion. It also requires careful handling because of the radioactivity and special procedures to dispose of the radioactive materials.

The presence of an AHH-inducing chemical in a sample can be determined by its ability to induce AHH in various types of cells. Once such cell culture assay is described in Bradlaw and Casterline, *J. Assoc. Off. Anal. Chem.*, 62:904–916 (1979). The method is a cell culture-enzyme induction bioassay, which uses the induction of AHH activity in rat hepatoma cell line H4IIE to detect minute amounts of dibenzodioxins, dibenzofurans, and biphenyls. The authors state that the assay is a useful system for screening large numbers of specially prepared food extracts for contamination by these compounds, but that the system may not be able to specifically identify the reactive substance or substances. Thus, the system may be useful for identifying the presence of AHH-inducing chemicals in a sample, but it cannot be used to identify and quantify a particular AHH-inducing chemical, such as TCDD.

SUMMARY OF THE INVENTION

As demonstrated in the Description of the Preferred Embodiments, below, I have invented an extremely sensitive and specific bioassay for particular toxic chemicals, which involves the modulation of enzyme activity induced by the toxic chemical by antibodies to that chemical. The invention overcomes the disadvantages of existing assays by being faster, cheaper, safer, and more sensitive and specific.

It is accordingly an object of this invention to provide a method of determining the concentration of an enzyme-inducing chemical in a sample. Additional objects and advantages of the invention will be set forth in part in the description that follows and in part will be obvious from the description or may be learned from practice of the invention. The objects and advantages may be realized and obtained by means of the instrumentalities and combinations particularly pointed out in the appended claims.

To achieve the objects and in accordance with the purpose of the invention, disclosed herein is a method of determining the concentration of an enzyme-inducing chemical in a sample by:
  (a) determining the concentration of all enzyme-inducing chemicals in a first portion of the sample;
  (b) contacting a second portion of the sample with antibodies to the enzyme-inducing chemical to form complexes of the chemical and the antibodies;
  (c) determining the concentration in the second portion of the sample of all enzyme-inducing chemicals that have not formed complexes; and
  (d) determining the concentration of the chemical in the sample by subtracting the concentrations of the chemicals as determined by step (c) from the concentration of the chemicals as determined by step (a),
wherein the concentrations of the chemicals in the first and second portions are determined by contacting the portions with cells that contain an inducible enzyme, determining the percent induction of the enzyme in the cells, comparing the percent induction to a standard curve of percent induction of the enzyme in the cells by a range of known concentrations of the chemical, and extrapolating the concentrations from the standard curve.

In a preferred method, the enzyme-inducing chemical is a dibenzodioxin, and in a particularly preferred method the enzyme-inducing chemical is 2,3,7,8-tetrachloro-dibenzo-p-dioxin.

The accompanying figures, which are incorporated in and constitute a part of the specification, illustrate an embodiment of the invention and, together with the description, serve to explain the principles of the invention.

DESCRIPTION OF THE PREFERRED EMBODIMENTS

Figure 1:
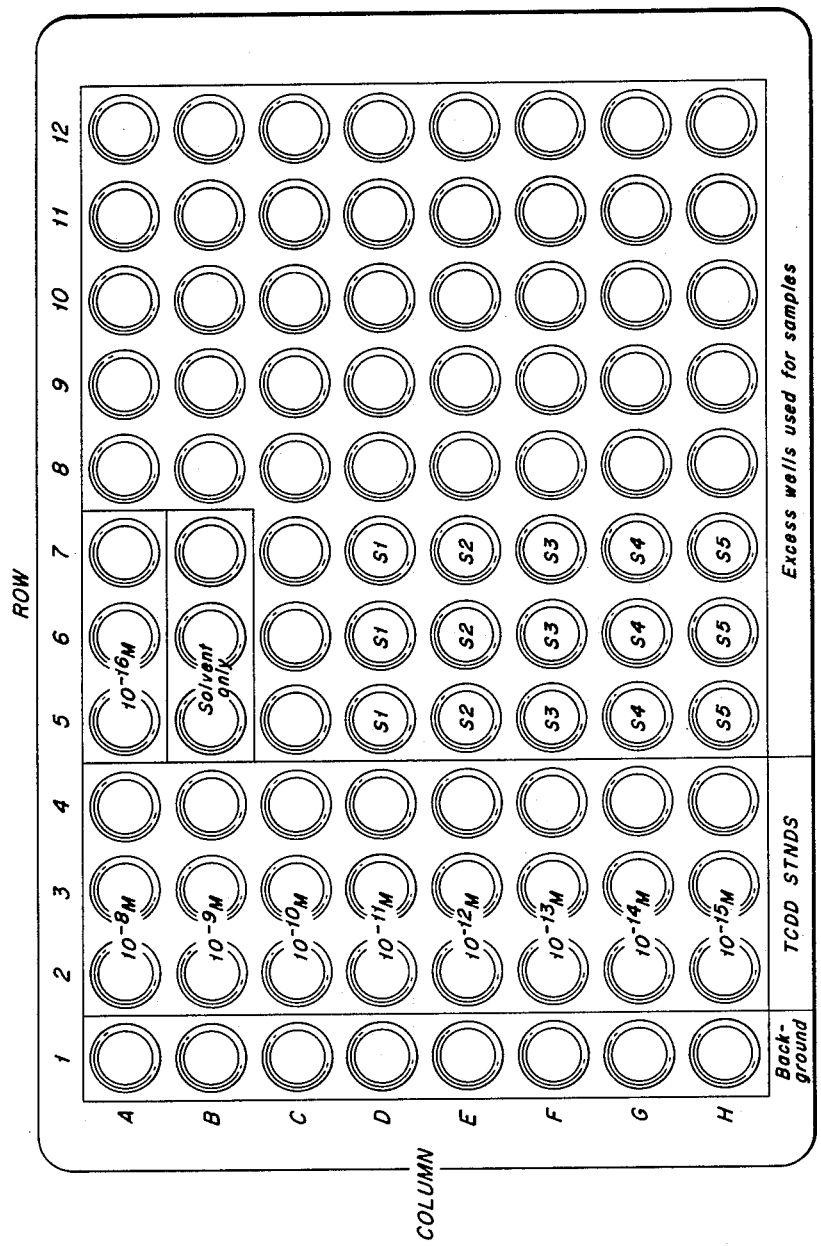
FIG. 1 is a photo/schematic of a microtiter plate which can be used in the practice of the present invention.

Reference will now be made in detail to the presently preferred embodiments of the invention, which, together with the following examples, serve to explain the principles of the invention As noted above, the present invention relates to a method of determining the concentration of an enzyme-inducing chemical, such as a toxicant, in a sample. It involves the use of an antibody to a toxicant to modulate enzyme activity induced by that toxicant in living cells. This leads to an extremely sensitive and specific assay for that toxicant.

An assay based on the inducibility of a particular enzyme or group of enzymes by a particular chemical in living cells can be an extremely sensitive assay for that chemical, but it does not discriminate among similar chemicals of the same type. If one wishes to detect and measure the concentration of a particular chemical in a sample, such as soil, it is usually contaminated by a mixture of chemicals of the same type or class. An enzyme induction assay is not sufficiently specific to distinguish among the several, similar chemicals. For example, the results of an enzyme induction assay for TCDD will be significantly affected by the presence of other chlorinated dibenzodiozins or other enzyme-inducing chemicals.

The present invention uses antibodies to the particular chemical sought to be identified and measured, such as TCDD, in order to provide specificity to the assay. This is accomplished by comparing the percent induction of the enzyme in cells by enzyme-inducing chemicals in the sample before and after the antibodies to the particular chemical sought to be detected have been added to the sample. The percent inductions are then compared to a standard curve created by measuring the percent inductions by known concentrations of the enzyme-inducing chemical. This permits the determination of the concentration of the enzyme-inducing chemical before and after the addition of the antibodies. Since the antibodies bind the chemical, it cannot induce the enzyme. Thus, a difference in the two concentrations signals the presence of the chemical sought to be detected, and the amount of the difference represents the concentration of the chemical. On the other hand, equal induction by an unknown in the presence and absence of antibodies to the chemical in question means the sample does not contain that chemical. Moreover, induction in the absence, but not the presence, of the antibodies means the sample is entirely that of the chemical in question. Induction in the absence, and partial induction in the presence of, the antibodies indicates the presence of a mixture of compounds in the sample.

Thus, by comparing the amount of induction mediated by the unknown to the induction mediated by the standard chemical concentrations, the level of the chemical in the sample can be determined, based upon the antibody's inhibition of induction. This assay permits the detection of an enzyme-inducing chemical in concentrations as low as 1 part per quadrillion.

In particular, the method of the present invention comprises the steps of:

(a) determining the concentration in a first portion of the sample of all chemicals that induce an enzyme in a cell or cells;

(b) contacting a second portion of the sample with antibodies to the chemical to form complexes of the chemical and the antibodies;

(c) determining the concentration in the second portion of the sample of all chemicals that induce the enzyme in the cell or cells; and (d) determining the concentration of the chemical in the sample by subtracting the concentrations of the chemicals as determined by step (c) from the concentration of the chemicals as determined by step (a), wherein the concentration of the chemicals in the first and second portions are determined by contacting the portions with cells that contain an inducible enzyme, determining the percent induction of the enzyme in the cells, comparing the percent induction to a standard curve of percent inductions of the enzyme in the cells by a range of known concentrations of the chemical, and extrapolating therefrom.

The sample may be any material, such as food, soil, ground water, or body fluids or tissues, which may be suspected of being contaminated with one or more enzyme-inducing chemicals. The sample is prepared for analysis by techniques well-known in the art so that the ultimate sample to be tested by the bioassay of the present invention is in liquid form and the enzyme-inducing chemical is dissolved in the sample. For example, material containing TCDD can be prepared for analysis according to the methods described in an Environmental Protection Agency study titled the *National Dioxin Study*, (EPA/600/3-85/019, April 1985), incorporated herein by reference.

Part of the preparation of a sample containing a chemical such as TCDD involves dilution until the TCDD is in solution. This occurs at a concentration of approximately 200 parts per trillion for TCDD.

Once the sample has been prepared, a portion of the sample is taken so that the concentration of the enzyme-inducing chemical in it can be determined by contacting the sample with the indicator cells. This step actually determines the concentration of all chemicals in the sample that induce the particular enzyme (or class of enzymes) in the indicator cells. For example, if the percent induction of aryl hydrocarbon hydroxylase is being measured, the sample may contain many related compounds that would induce this family of enzymes. However, if only one particular chemical were being sought, such as TCDD, the concentration of that chemical alone could not yet be determined by this step. Thus, at this point, the concentration of all of the chemicals in the first portion of the sample is determined by contacting that portion with the indicator cells and determining the percent induction of the enzyme in the cells.

The percent induction is then compared with a standard curve of the percent inductions of the enzyme in the cells by a range of known concentrations of the chemical sought to be detected and measured By extrapolating from the standard curve, the total concentration of chemicals in the unknown, which induce the particular enzyme, can be determined. That is, the first portion will have a concentration of enzyme-inducing chemicals equal to the concentration of the known chemical giving the same percent induction on the standard curve.

A second portion of the sample is then mixed with antibodies to the chemical sought to be detected and measured. This permits the formation of complexes between the antibodies and the chemical. When the chemical is bound to the antibodies, it cannot induce the enzyme in the cells. The percent induction of the enzyme in the indicator cells of this portion is then measured and compared to the standard curve. The concentration of enzyme-inducing chemicals is again determined. This is the concentration of the related, but interfering chemicals. If there are no such chemicals, the concentration of this step will be zero.

The concentration of the chemical sought to be detected and measured is then determined by subtracting the concentrations of the chemicals in the second portion as determined by the third step from the concentrations of the chemicals in the first portion determined by the first step.

The preparation of a standard curve of the percent inductions of known concentrations of the chemical is done by techniques known in the art. Such standardization may be done before, during, or after the evaluation of the sample containing the unknown.

The first and second portions of the sample, as well as the preparations used in generating the standard curve, are left in contact with the indicator cells for a time sufficient for enzyme induction Generally, this is approximately 4 to 20 hours.

The method of the present invention can be applied to any enzyme-inducing chemical. An enzyme-inducing chemical is any chemical which, upon interaction with a living cell, causes that cell by one or more mechanisms to express a higher level of one or more cellular enzymes. In a preferred embodiment, the chemicals are alkyl or aryl hydrocarbon hydroxylase (AHH)-inducing chemicals. These are usually alkyl or aryl hydrocarbons, including the halogenated dibenzodioxins, dibenzofurans, biphenyls, azyoxybenzenes, and biphenylenes. Preferably, the AHH-inducing chemicals detected and measured by the present invention are halogenated dibenzodioxins or polychlorinated biphenyls. Most preferably, the chemical is 2,3,7,8-tetrachloro-dibenzo-p-dioxin (TCDD). It should be noted that the method can be used to detect more than one enzyme-inducing chemical in a sample by using antibodies to each chemical sought to be detected Any living cell that is capable of enzyme induction by a chemical sought to be determined and measured may be used as an indicator cell. Generally, such cells will be mammalian or other animal cells that are capable of growing in culture and are capable of efficient enzyme induction. For AHH induction, liver cells are preferred. Particularly preferred is the rat hepatoma cell line H4IIE, which is commercially available from the American Type Culture Collection (ATCC), 12301 Parklawn Drive, Rockville, Md. U.S.A. 20852 as cell line CRL 1548, and which was redeposited on Aug. 21, 1986 under the ATCC Accession Number CRL 9185. For a more detailed description of this cell line, see Bradlaw and Casterline, *J. Assoc. Off. Anal. Chem.*, 62:

904–916 (1979), which is specifically incorporated herein by reference.

The induction of the enzyme or group of related enzymes, such as AHH, may be measured by techniques known in the art. Also, any of the AHH enzymes may be measured. Preferably, induction is measured by measuring the induction of 7-ethoxyresorufin-O-deethylase (EROD), which, in turn, may be measured by the conversion of 7-ethoxyresorufin (ER) to resorufin, which EROD catalyzes. This reaction may be measured spectrometrically at 572 mm according to the technique of Klotz et al., *Anal Bioch.*, 140: 138–145 (1984), or spectrofluorimetrically by the method of Prough et al. *Meth. Enzymol.* 52: 372–377 (1978), both of which are specifically incorporated herein by reference. A side reaction, the reduction of resorufin by quinone oxidoreductase, is inhibited by the inclusion of 10 micromolar dicumarol in the reaction mixture as disclosed in Nims et al., *Arch. Bioch. Biophys.*, 229: 459–465 (1984), which is incorporated herein by reference. As previously mentioned, induction is measured after the sample has been in contact with the cells from about 4 to about 24 hours. Cell line H4IIE, mentioned above, has low basal levels of EROD, but the EROD is induced by sub-nanomolar concentrations of chemicals such as TCDD, which is one reason why this cell line is particularly preferred.

The antibodies used in the assay may be polyclonal or monoclonal antibodies. Polyclonal antibodies may be prepared by techniques known in the art. See Albro et al., *Toxicol. Appl. Pharmacol.*, 50: 137 (1979) and Albro et al., in *Meth. Enzymol.* (J. L. Langone and H. van Vunakis, eds.), Vol. 84, pp. 619–628, (Academic Press, New York, 1982) which are incorporated herein by reference Polyclonal antibodies are preferred if a class or group of AHH-inducing chemicals are sought to be detected. Monoclonal antibodies are preferred when a particular chemical is sought to be detected because of their greater specificity. In addition, monoclonal antibodies will be generally preferred because the source is more constant and reliable, and they are easier to standardize.

The preparation of monoclonal antibodies to AHH-inducing chemicals requires special techniques to overcome special problems. Such antibodies may be prepared using the methods disclosed in the U.S. patent application of Kenneth W. Hunter, Ser. No. 899,163, filed Aug. 8, 1986, Monoclonal Antibodies Reactive with Chlorinated Dibenzo-p-Dioxins and Methods of Preparing and Using Same, which has been filed concurrently herewith and is specifically incorporated herein by reference.

It is to be understood that the application of the teachings of the present invention to a specific problem or environment will be within the capabilities of one having ordinary skill in the art in light of the teachings contained herein. An example of the method of the present invention appears as follows.

EXAMPLE

Antibody-Based Bioassay for TCDD

Materials

The following chemicals were used in the bioassay: TCDD (Kor Isotopes, Cambridge, Mass., supplied 1 mg/ml in anisole); Dimethylsulfoxide (DMSO); Ethoxyresorufin (ETR) (Molecular Probes, Inc., Junction City, Oreg., Cat #R-352); Dicumarol (Sigma Chemical Co., St. Louis, Mo., Cat #M 1390, as 3,3'-methylene-bis-(4-hydroxycoumarin).

The following biological reagents were used: Williams Medium E (WME, Gibco, Grand Island, N.Y.) supplemented with L-glutamine (2 mM) and HEPES buffer pH 7.3–7.4 (10 mM) and 10% fetal bovine serum (FBS, GIBCO), which is designated complete WME; H4IIE rat hepatoma cells (*J. Assoc. Off. Anal. Chem.* 62:904, 1979; *Tox. Let.* 13:87, 1982), available from the American Type Culture Collection, Rockville, Md., as cell line CRL 1548 or cell line CRL 9185; and Tris (0.05M)—Sucrose 0.2M) buffer pH 7.6–7.8, designated Tris-Sucrose.

The following equipment was used to perform the bioassay: Bio-Tek EIA Reader, Model 310, equipped with 570 nM filter; and 96 well tissue culture dishes (Falcon #3072), with a 12 by 8 array of wells.

Procedure

On the first day, H4IIE cells from a culture in log-phase of growth were plated in a 96 well dish at $5 \times 10^4$ cells/well in 250 microliters of complete WME. The next day each well was refed with 270 microliters of complete WME. On day 3, each well was refed with medium containing TCDD from $10^{-8}$M to $10^{-16}$M.

The dilutions of TCDD and treatment of cells were done as follows. First, an aliquot of the TCDD stock (1000 micrograms per milliliter in anisole) was diluted to 3200 nanograms per milliliter in DMSO. At this time the concentration of anisole was 0.32%; of DMSO, 99.68%. The TCDD solution was then diluted to 32 nanograms per milliliter in complete WME (approximately $10^{-7}$M); final solvent concentrations: anisole=0.00329%; DSMO=0.9968%. Cells to be treated with TCDD standards were in rows A–H, columns 2–4, and row A, columns 5–7 of the 96 well dish (See FIG. 1). Thirty microliters of TCDD, $10^{-8}$M, were added to the cells in wells A 2–4, which already contained 270 microliters of complete WME. The TCDD concentration in these wells was $10^{-8}$. Thirty microliters from row A (3–5) was transferred to row B (3–5), and the solution was mixed with the pipette to ensure complete mixing. This was a 1:10 dilution, resulting in a molar concentration of TCDD in B (2–4) of $10^{-9}$. Thirty microliters from B (2–4) were transferred into C (2–4). The same transfer pattern was continued through row H, and then to A (5–7). Control wells received solvent only and were located in B 5–7. Unknown samples in solvents were diluted to bring solvent concentrations down to 0.1% or less, and solvent controls, containing the same concentration of solvent as the samples but without TCDD, were also tested. Unknowns were tested at a minimum of 4 different serial dilutions, prepared as described for the standards.

The cells were incubated for 24 hours.

On the fourth day the medium was removed, and the cells were washed twice with serum-free WME, once with tris-sucrose and refed with tris-sucrose supplmented with 10 micromolar dicumoral and 3.26 micrograms per milliliter ethoxyresorufin (ETR). Dicumoral stock solution was 3700 micrograms per milliliter in 0.1N NaOH which was then diluted 1:1100 in tris-sucrose for a final concentration of 10 micromolar; ETR stock solution was 652 micrograms per milliliter in ethanol. Five microliters per ml of tris-sucrose was added.

Wells A-1 through H-1 served as background controls and therefore receive no ETR; they received dicumarol in tris-sucrose.

The plate was placed in the Bio-Tek reader with 570 nM filter, set to read at 30 minutes. Blanking was set for A-1 through H-1.

The average OD 570 for each dilution of TCDD or unknown was calculated at time zero and again after 1 hour. The difference, designated delta-OD, was recorded.

The data from the known doses of TCDD were used to generate a curve from which the TCDD concentrations were calculated. The data were converted to a percent AHH induction for plotting, as shown in FIG. 2 (closed circles).

To confer specificity to the TCDD Bioassay, the following addition was made to the procedure described above. The treatment of cells with TCDD was the same except that, for standards and unknowns, a second set of treatments was done in which the dilutions of TCDD or unknowns were made with medium containing polyclonal anti-TCDD antibodies prepared in rabbits as described by Albro et al., *Methods in Enzymology*, 84: 619–628 (1982); Albro et al., *Toxicol. Appl. Pharmacol.*, 50:137–146 (1979), incorporated herein reference. The concentration of antibody used was that which caused at least a 50% reduction in EROD induction by TCDD at $10^{-9}$M, as determined in quality assurance tests. Quality assurance assays were performed by determining the antibody-mediated reduction in EROD induction by $10^{-9}$M TCDD for several concentrations of antibody.

Results

Figure 2:
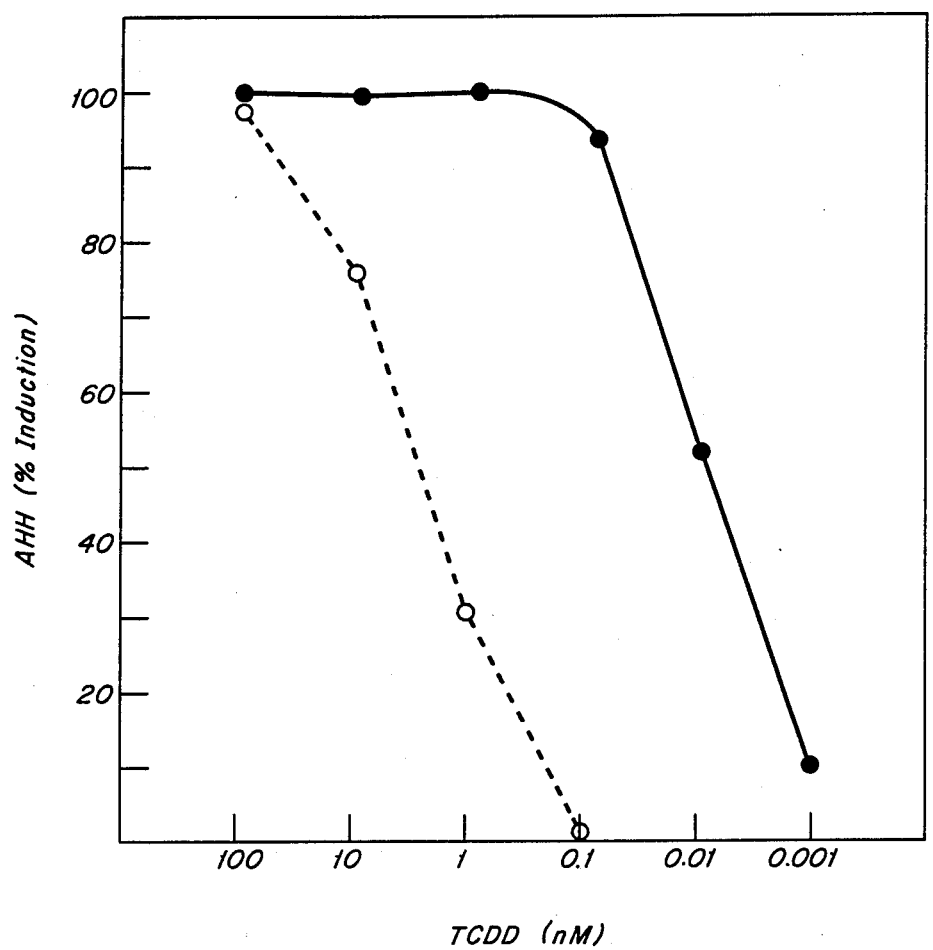
FIG. 2 illustrates a plot of data generated by the bioassay. The solid line represents the percent induction of 7-ethoxy-resorufin-O-deethylase at different concentrations of 2,3,7,8-tetrachloro-dibenzo-p-dioxin (TCDD). The dotted line represents the same dose response done in the presence of one microgram per milliliter of anti-TCDD antibody.

FIG. 2 shows a plot of experimental data for two standard curves, one run with TCDD alone (closed circles) and one run with TCDD plus polyclonal anti-TCDD antibody (open circles). At a TCDD concentration of 100 nM, there was no difference in the two curves, indicating that there was more TCDD than could be neutralized by this particular concentration of anti-TCDD antibody. However, at a TCDD concentration of 0.1 nM, near maximal induction of AHH was observed in the antibody untreated cells, whereas the anti-TCDD treated cells showed complete inhibition of AHH induction. This latter result indicated that all of the AHH induction was attributable to TCDD. Dilutions of an unknown sample run with and without anti-TCDD antibody can be compared to those standard curves to verify the identity of the inducer (e.g. TCDD), and to precisely determine its concentration, since the antibody will bind only to one chemical (e.g. TCDD) and not affect EROD induction by other compounds in the sample. Thus, if in the presence of an anti-TCDD antibody, all induction of EROD is eliminated, then any induction observed in the absence of antibody can be attributed to TCDD. Further, partial reduction of EROD induction by an anti-TCDD antibody indicates the presence of some TCDD in the sample. The induction difference for sample with and without antibody can be compared to a similar difference on the standard curve to obtain the concentration of TCDD in the sample. Finally, no difference in induction indicates that the sample contains no TCDD.

It will be apparent to those skilled in the art that modifications and variations can be made to the processes of the present invention. Thus, it is intended that the present invention cover modifications and variations of this invention, provided they come within the scope of the appended claims and their equivalence.

What is claimed is:

1. A method of determining the concentration of an enzyme-inducing chemical in a sample comprising the steps of:
    (a) determining the concentration of all enzyme-inducing chemicals that induce alkyl hydrocarbon hydroxylase or aryl hydrocarbon hydroxylase in a first portion of said sample;
    (b) contacting a second portion of said sample with antibodies to said enzyme-inducing chemical to be determined to form complexes of said chemical and said antibodies;
    (c) determining the concentration in said second portion of said sample of enzyme-inducing chemicals that have not formed said complexes; and
    (d) determining the concentration of said chemical in said sample by subtracting the concentrations of said chemicals as determined by step (c) from the concentration of said chemicals as determined by step (a),
wherein said concentrations of said chemicals in said first and second portions are determined by contacting said portions with cells that contain an inducible enzyme, said inducible enzyme being aryl hydrocarbon hydroxylase or alkyl hydrocarbon hydroxylase, determining the percent induction of said enzyme in said cells, comparing said percent induction to a standard curve of the percent induction of said enzyme in said cells by a range of known concentrations of said chemical, and extrapolating said concentrations from said standard curve.

2. The method of claim 1 wherein said antibodies are monoclonal antibodies.

3. The method of claim 1 wherein said enzyme-inducing chemical is a dibenzodioxin.

4. The method of claim 1 wherein said enzyme-inducing chemical is 2,3,7,8-tetrachloro-dibenzo-p-dioxin (TCDD).

5. The method of claim 1 wherein said enzyme-inducing chemical is a polychlorinated biphenyl.

6. The method of claim 1 wherein said cells are rat hepatoma cells.

7. The method of claim 1 wherein said enzyme-inducing chemical is an alkyl hydrocarbon hydroxylase-inducing chemical and said inducible enzyme is alkyl hydrocarbon hydroxylase.

8. The method of claim 1 wherein said enzyme-inducing chemical is an aryl hydrocarbon-inducing chemical and said inducible enzyme is aryl hydrocarbon hydroxylase.

9. The method of claim 1 wherein said inducible enzyme is 7-ethoxyresorufin-O-deethylase (EROD).

10. The method of claim 9 wherein said enzyme inducing chemical is TCDD.

11. The method of claim 9 wherein determining the induction of EROD comprises measuring the conversion of 7-ethoxyresorufin to resorufin by EROD.

12. The method of claim 11 wherein said measuring comprises spectrophotometrically determining the concentration of said resorufin.

13. The method of claim 1 wherein said enzyme-inducing chemical is TCDD and said antibodies are monoclonal antibodies to TCDD.

14. A method of determining the concentration of an aryl or alkyl hydrocarbon hydroxylase (AHH)-inducing chemical in a sample comprising the steps of:
    (a) contacting a range of known concentrations of said AHH-inducing chemical with cells that contain AHH;

(b) determining the percent induction of AHH in said cells by each of said known concentrations of said chemical;

(c) contacting a first portion of said sample with said cells;

(d) determining the percent induction of AHH in said cells by said first portion;

(e) determining the total concentration of AHH-inducing chemicals in said sample by comparing said percent induction of AHH by said first portion to the percent inductions of AHH in said cells by said known concentrations of said AHH-inducing chemical;

(f) contacting a second portion of said sample with antibodies to said AHH-inducing chemical;

(g) repeating steps (c)-(e) with said second portion; and (h) determining the concentration of said AHH-inducing chemical in said sample by substracting the concentration of AHH-inducing chemicals as determined by step (g) from the concentration of AHH-inducing chemicals as determined by step (e).

15. The method of claim 14 wherein said antibodies are monoclonal antibodies.

16. A method of determining the concentration of TCDD in a sample, comprising the steps of:

(a) determining the concentration of all AHH-inducing chemicals in a first portion of said sample;

(b) contacting a second portion of said sample with monoclonal antibodies to TCDD to form complexes of TCDD and said antibodies;

(c) determining the concentration in said second portion of said sample of all AHH-inducing chemicals that have not formed said complexes; and (d) determining the concentration of TCDD in said sample by substracting the concentration of said AHH-inducing chemicals as determined by step (c) from the concentration of all AHH-inducing chemicals as determined by step (a), wherein said concentrations of said chemicals in said first and second portions are determined by contacting said portions with cells from a rat hepatoma cell line H4IIE, determining the percent of AHH induction in said cells, comparing said percent induction to a standard curve of percent inductions of AHH in said cells by a range of known concentrations of TCDD, and extrapolating said concentrations from said standard curve, said percent inductions of AHH being determined by measuring the conversion of 7-exthoxyresorufin to resorufin by EROD by spectrophotometrically determining the concentration of resorufin in said cells.

* * * * *